United States Patent [19]

Gibbs

[11] Patent Number: 4,701,850
[45] Date of Patent: Oct. 20, 1987

[54] METHOD AND APPARATUS UTILIZING AGAR DIFFUSION TECHNIQUE FOR DETERMINING QUANTITATIVE DRUG CONCENTRATION PARAMETER

[76] Inventor: David L. Gibbs, 250 Mercer St., A301, New York, N.Y. 10012

[21] Appl. No.: 749,006

[22] Filed: Jun. 26, 1985

[51] Int. Cl.⁴ .............................................. G06F 15/42
[52] U.S. Cl. .................................... 364/415; 435/291; 435/32
[58] Field of Search ........................ 435/29, 32, 34, 39, 435/287–291; 364/415, 562; 33/143 D, 143 L

[56] References Cited

U.S. PATENT DOCUMENTS

| | | | |
|---|---|---|---|
| 3,649,460 | 3/1972 | Controni et al. | 435/34 |
| 3,819,490 | 6/1974 | Klingstrom et al. | 435/32 |
| 4,021,308 | 3/1977 | Saxholm | 435/32 |
| 4,221,867 | 9/1980 | McFadden | 435/32 |
| 4,586,150 | 4/1986 | Budziak | 364/562 |

OTHER PUBLICATIONS

Sautter et al, "Comparison of Biogram and Commercial Microdilational Antimicrobial Susceptibility Test Systems", *Journal of Clinical Microbiological*, Feb. 1987, pp. 301–304.
"Evaluation of the Biogram Antimicrobial Susceptibility Test System", *Journal of Clinical Microbiology*, Nov. 1985, pp. 793–798, D'Amato et al.
"Antimicrobic Susceptibility Testing: A New Method", *Clinical Lab Products*, Nov. 1985, pp. 21–23.
Ellner et al., "The Inhibitory Quotient", *JAMA*, Oct. 2, 1981, vol. 246, No. 14, pp. 1575–1578.
Barry et al, "Evaluation of the Micro–Media System for Quantitative Antimicrobial Drug Susceptibility Testing", *Antimicrobial Agents and Chemotheraphy*, Jan. 1978, pp. 61–69.

Primary Examiner—Jerry Smith
Assistant Examiner—Gail Hayes
Attorney, Agent, or Firm—Kenyon & Kenyon

[57] ABSTRACT

An apparatus for using the continuous-gradient disk diffusion technique to obtain quantitative minimum inhibitory concentrations and inhibitory quotients comprises an electronic caliper operatively coupled to a microprocessor for feeding thereto signals coding the diameters of bacteria-growth inhibition zones measured by the caliper. In response to the signals, the microprocessor automatically calculates by means of a regression-type analysis the minimum inhibitory concentrations of the drugs, as determinable based on a correlation with results by a broth dilution test, with respect to the bacterium under study. The microprocessor also calculates, in response to the signals from the electronic caliper, inhibitory quotients with respect to a plurality of different body fluids such as bile, blood and cortical spinal fluid. The apparatus may also be used to determine unknown concentrations of antimicrobial drugs by using the disk diffusion technique and a regression analysis.

29 Claims, 5 Drawing Figures

METHOD AND APPARATUS UTILIZING AGAR DIFFUSION TECHNIQUE FOR DETERMINING QUANTITATIVE DRUG CONCENTRATION PARAMETER

BACKGROUND OF THE INVENTION

This invention relates to a method and apparatus utilizing a continuous-gradient agar diffusion technique for determining a drug concentration parameter. More particularly, this invention relates to such a method and apparatus for determining a minimum inhibitory concentration of an antimicrobial drug required to substantially prevent the growth of a bacterium. In addition, or alternatively, the drug concentration parameter determined by the method and apparatus of this invention may be an unknown concentration of an antimicrobial drug taken, for example, from a body fluid or tissue sample or from a laboratory preparation.

Most clinical microbiology laboratories in the United States and in other countries throughout the world use the agar disk-diffusion method for determining the susceptibility of microorganisms, i.e., bacteria, to various antimicrobial drugs. In the agar disk-diffusion method, a sample of a bacterium, for example, from a body fluid of a patient is placed on the surface of an agar nutrient medium along with several small absorbant paper disks each containing a predetermined amount of a respective antimicrobial drug. The bacteria sample is then permitted to incubate for a number of hours to form a bacterium culture on the surface of the agar medium. During the incubation period, the drugs in the paper disks diffuse outwardly therefrom through the agar medium. If the bacterium being tested is susceptible to a particular antimicrobial drug, the growth of the bacterium is substantially prevented or inhibited within a circular zone surrounding the respective drug-carrying disk, the radius or diameter of the inhibition zone being a function of the degree of susceptibility of the bacterium to the particular drug.

The results of conventional methods utilizing the disk diffusion technique are invariably qualitative. The degree of susceptibility of a tested bacterium to an antimicrobial agent is characterized as "susceptible," "moderately susceptible," "intermediate" or "resistant" by a medical technician, depending on the relative size of the inhibition zone surrounding the disk carrying the antimicrobial agent. For example, if the diameter of the bacteria-growth inhibition zone for a particular drug is relatively small, the bacterium under study is characterized as "resistant." In contrast, if a bacteria-growth inhibition zone surrounding a disk is relatively large, the bacterium under study is characterized as "susceptible."

In another method for determining the susceptibility of a bacterium to an antimicrobial drug, known as the "dilution" method, samples of the bacterium under test are placed in respective nutrient solutions which contain respective concentrations of the antimicrobial drug. The drug concentrations are varied in a regular fashion. The dilution method yields a quantitative value of a minimum inhibitory concentration of the antimicrobial drug with respect to the tested bacterium. This minimum inhibitory concentration is the least concentration of the antimicrobial drug which substantially prevents or inhibits the growth of the bacterium. The minimum inhibitory concentration is determined, in accordance with the dilution method, by simply identifying the receptacle with the least drug concentration which exhibits no bacterial growth.

The dilution method is advantageous in that it provides quantitative antimicrobial susceptibility test results. However, the dilution testing method is usually substantially more expensive than the disk diffusion method, inasmuch as quantitative dilution testing requires expensive materials, expensive instrumentation and retraining of laboratory personnel. Moreover, in practice, the number of concentrations tested is often reduced in order to make room for the testing of a greater number of antimicrobial drugs on a microdilution panel (an array of solution receptacles). It has also been discovered that the quality of the results from the dilution testing method is difficult or impossible to control if the number of dilutions per drug is reduced substantially.

It is to be noted that the dilution method measures bacterial susceptibility on a discrete scale, interrupted by dilution intervals, while the disk diffusion method is capable of measuring bacterial susceptibility on a continuous scale. Thus, the disk diffusion method provides a potential for greater accuracy and reliability in the measurement of bacteria susceptibility to antimicrobial agents than is possible with the dilution method.

Correlation coefficients between zone diameters determined by the disk diffusion method and minimum inhibitory concentrations determined by the dilution method are published for most antimicrobics early in their development. The coefficients clearly demonstrate a close correlation between the disk diffusion method and a painstakingly executed dilution method performed with small steps between the dilutions.

In reports on the results of disk diffusion tests, the terms "susceptible" and "resistant" are used without reference to a specific concentration of the antimicrobial agent under consideration. The terms mislead many to believe that bacteria are inherently susceptible or resistant to all drugs. Moreover, the qualitative nature of these terms allows no distinction between varying degrees of susceptibility and makes it exceeding difficult for a clinician to know whether he is likely to achieve a concentration of the drug that will exceed the minimum inhibitory concentration in the body tissue harboring an infection.

The "breakpoints" in the discontinuous qualitative categories of conventional disk diffusion test results are determined essentially arbitrarily. Widespread disagreement over which "breakpoints" to use results in widespread discrepancies in results reported to physicians.

Each antimicrobial chemical has a usual concentration in each of the major body fluids, based on a given usual drug dosage, i.e., in blood, the bile, the urine and the cerebral spinal fluid. The ratio between the usual concentration at the lowest usual dosage of an antimicrobial drug in a body fluid to the minimum inhibitory concentration of that drug for a particular bacterium provides an especially useful quantitative indication of the expected effectiveness of that drug in combating the presence of the bacterium in that body fluid. This ratio is called an "inhibitory quotient." The higher the inhibitory quotient, the more likely it is that the respective drug will be successful in eradicating the existence of the invading microorganism in the respective body fluid or in a body tissue capable of sustaining a drug concentration predictably related to the maximum concentration in the body fluid. Thus, inhibitory quotients enable the physician to determine the probability that the concentration of a particular potentially administerable antimicrobial will exceed the minimum inhibitory concentration at the site of the infection. The calculation of inhibitory quotients facilitates the comparison of the relative activity of various drugs in different body tissues. Generally, higher dosages result in higher inhibitory quotients which indicate higher tissue concentrations.

An object of the present invention is to provide a method and an associated apparatus which use the agar diffusion technique to determine a quantitative drug concentration parameter.

Another, more particular, object of the present invention is to provide such a method and such an associated apparatus for quantitatively gauging the susceptibility of a microorganism such as a bacterium to an antimicrobial agent.

Another particular object of the present invention is to provide such a method and such an apparatus for determining unknown concentrations of particular antimicrobial drugs.

Another object of the present invention is to provide such a method and such an apparatus which are inexpensive and easy to use.

A more particular object of the present invention is to provide such a method and such an apparatus for making quantitative determinations of minimum inhibitory concentrations of one or more drugs with respect to a microorganism and for making further quantitative determinations of inhibitory quotients.

SUMMARY OF THE INVENTION

A medical testing apparatus in accordance with the invention is utilizable with the agar diffusion technique for determining a quantitative drug concentration parameter related to the size of a bacteria-growth inhibition zone on a nutrient medium. The zone surrounds a drug-carrying paper disk or a hole or well in the nutrient semi-solid medium on which a bacteria culture is grown. The apparatus comprises a distance-measuring device, a computer or microprocessor and an electrically conductive link for coupling the distance-measuring device to the computer. The distance-measuring device preferably includes an electronic caliper for measuring a linear dimension (e.g., a diameter or a radius) of the bacteria-growth inhibition zone and for generating a signal coding the measured value of the linear dimension. In response to the signal carried from the distance-measuring device over the electrically conductive link, the computer or microprocessor automatically calculates the quantitative drug-concentration parameter. The electronic caliper is provided with a manually actuatable switch for inducing transmission of the measurement signal over the conductive link to the computer.

Where the calculated parameter is a minimum inhibitory concentration of a drug, a memory in the computer stores, in digitally encoded form, information for defining a linear relationship between the size of a bacteria-growth inhibition zone for the drug, as defined by the linear dimension of the zone, and the concentration of the drug in solution.

Preferably, the memory stores such information for a multiplicity of different antimicrobial drugs and further stores, in digitally encoded form, usual achievable concentrations of each of the antimicrobial drugs in a multiplicity of different body fluids. The memory advantageously stores, in addition, a drug cost category factor.

An input device such as a keyboard is operatively connected to the computer for instructing the computer to automatically calculate, in response to signals from the distance-measuring device, a minimum inhibitory concentration and a plurality of inhibitory quotients for one or more antimicrobial drugs selected by means of the input device.

In operating the apparatus in accordance with the invention, the jaws of the electronic caliper are manipulated so that the spacing between the jaws is approximately equal to a linear diametrically oriented dimension of the bacteria-growth inhibition zone surrounding a drug-carrying receptacle in the form of a disk or hole. The caliper is then operated to automatically generate and transmit to the computer a signal coding the dimension measured by manipulating the jaws of the caliper. Upon receiving the signal from the caliper, the computer automatically calculates a drug-concentration parameter, e.g., a minimum inhibitory concentration or an unknown concentration of an antimicrobial drug.

In accordance with another feature of the present invention, the apparatus may be used to determine an unknown concentration of an antimicrobial drug by measuring the diameters of the inhibition zones about disks or holes carrying known quantities of the antimicrobial drug under consideration. In response to signals from the electronic caliper and from the input device, the computer automatically generates a regression line or mathematical function wherein the known amounts are paired with respective zone sizes. The regression line or function is used by the computer to generate a value for the unknown concentration from the signal coding the diameter of an inhibition zone about a disk or hole carrying the unknown concentration.

An apparatus and a method in accordance with the invention are utilizable to simply, inexpensively and rapidly derive both quantitative and interpreted results from the agar diffusion technique. The simplicity, economy, reproducibility and accuracy of the agar diffusion method are retained, while the testing time is reduced and easily interpreted quantitative results are reported. Time and materials cost savings over the dilution method are substantial.

The present invention enables the quantitative measurement, on a continuous scale, of bacterial susceptibility to antimicrobials. Moreover, the accuracy of the results can be ensured by performing a simple check involving disks from the same batches as the disks used to determine the susceptibility of the bacterium under study. The quality-control disks are disposed on an agar medium from the same source as the agar medium on which the sample culture is placed.

An apparatus in accordance with the present invention is provided with a printer operatively connected to the computer or microprocessor for printing out drug names, minimum inhibitory concentrations and inhibitory quotients. Further information, such as drug costs, may also be printed.

The results of the automatic agar disk diffusion method in accordance with the invention are quantitative and enable the physician to select the most active, least toxic and inexpensive antimicrobic, whereby unnecessary use of the most expensive drugs can be reduced.

DETAILED DESCRIPTION

Figure 1:
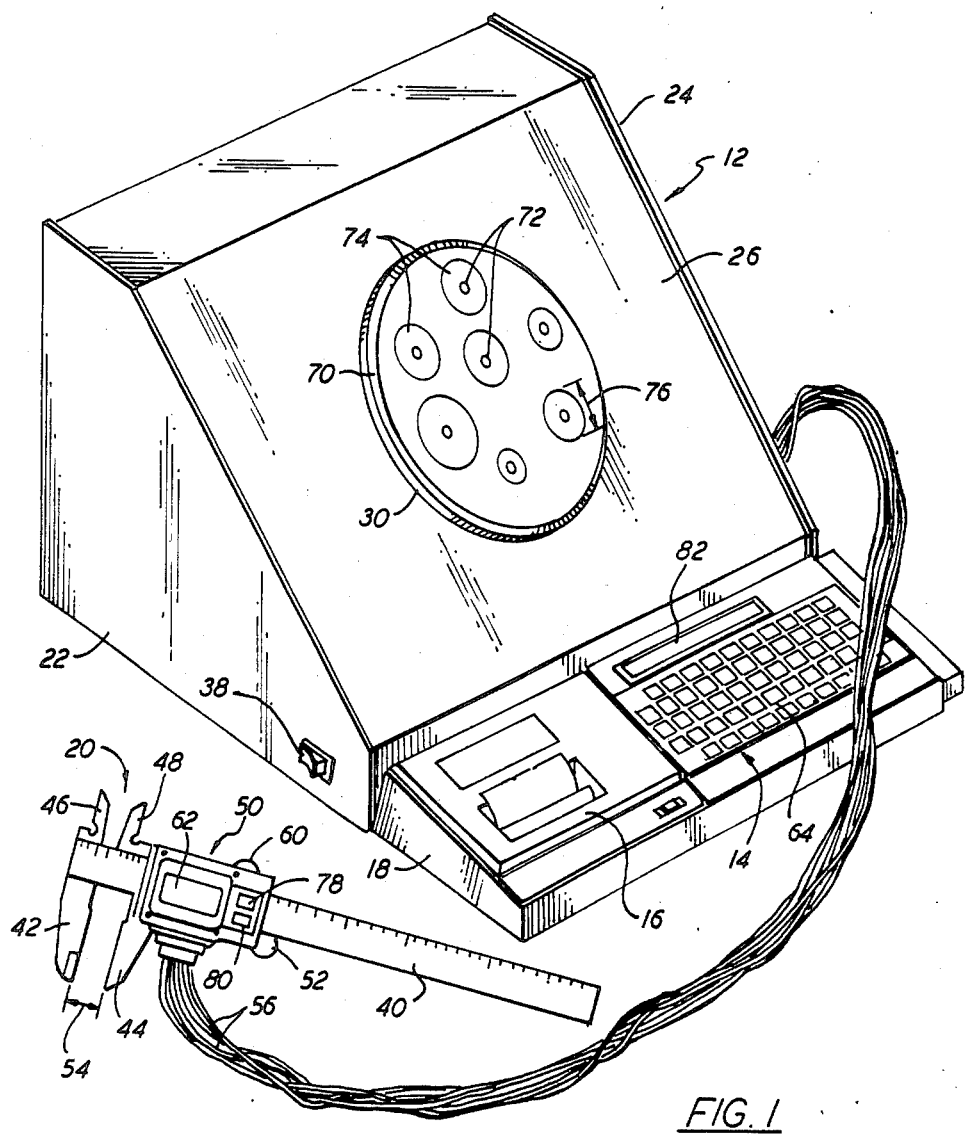
FIG. 1 is an isometric view of an apparatus in accordance with the present invention, showing a housing, an electronic caliper and a microprocessor with a keyboard.

As illustrated in FIG. 1, an apparatus adapted for utilization of the continuous-gradient agar diffusion technique for making a quantitative determination of the susceptibility of a microorganism, i.e., a bacterium, to an antimicrobial chemical or drug comprises a housing 12, a computer or microprocessor 14, a printer 16, a frame 18 supporting the printer 16 and the microprocessor component 14, and a distance measuring device in the form of an electronic or digital caliper 20.

Figure 2:
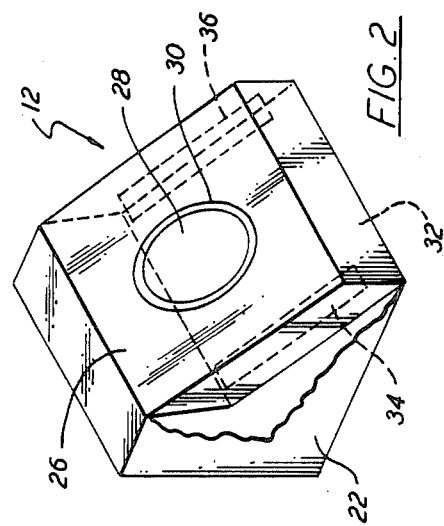
FIG. 2 ia an isometric view of the housing of FIG. 1.

As illustrated in FIGS. 1 and 2, housing 12 includes a pair of generally triangular upright members 22 and 24 between which is supported an inclined support plate 26. Support plate 26 is provided with a circular or square transparent region 28 surrounded by an annular lip 30. Inclined plate 26 forms an upper wall of a generally prismatic inclined chamber having a bottom wall formed by an inclined partition 33 extending generally parallel to inclined plate 26. Disposed within the chamber at opposite ends thereof, proximately to upright members 22 and 24, are a pair of elongate standardized light sources 34 and 36 connected to a power source (not illustrated) by means of a toggle switch 38.

Housing 12 may be detachably connectable to frame 18 and computer or microprocessor 14 may also be removably mounted to frame 18.

As illustrated in FIG. 1, electronic caliper 20 comprises an elongate rail 40 provided with distance markings in the manner of a ruler. Caliper 20 is provided with a first pair of measurement jaws 42 and 44 disposed along one edge of rail 40 and a second pair of jaws 46 and 48 disposed along an opposite edge of the rail. Jaws 42 and 46 are fixed to rail 40, while jaws 44 and 48 are fixed to a carriage member 50 shiftably mounted to rail 40. The position of carriage 50 and jaws 44 and 48 along the length of rail 40 is adjusted by means of a thumb screw 52 threadedly engaging a row of teeth (not illustrated) along an edge of rail 40. Carriage 50 houses an electronic sensing device for monitoring the position of the carriage and jaws 44 and 48 along rail 40. The electronic sensing device (not illustrated) produces an electrical signal coding the distance 54 between jaws 42 and 44 and between jaws 46 and 48, the spacing between jaws 42 and 44 being equal to the spacing between oppositely facing edges of jaws 46 and 48.

Figure 3:
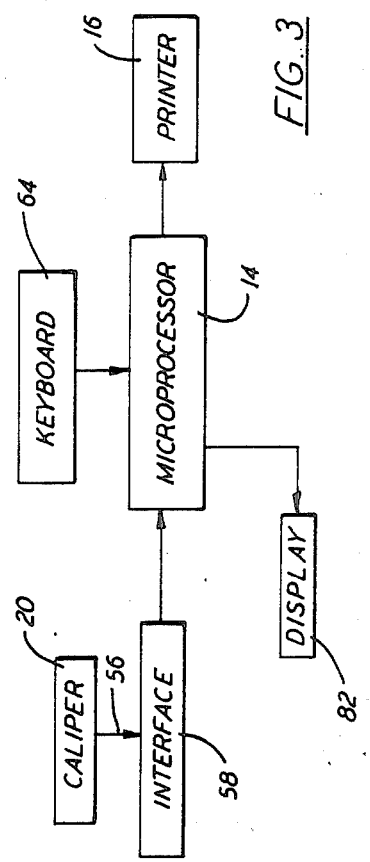
FIG. 3 is a block diagram showing the connection between the caliper and microprocessor of FIG. 1.

As illustrated in FIGS. 1 and 3, electronic caliper 20 and, in particular, the electrical sensing device housed in carriage 50 are connected to microprocessor 14 by one or more leads 56 and an electronic interface 58 disposed inside housing 12. Upon the actuation of a pushbutton switch 60 on carriage 50, the signal coding the distance 54 between caliper jaws 42 and 44 is transmitted to microprocessor 14 via coupling leads 56 and interface 58.

Carriage 50 of caliper 20 is provided with a digital liquid crystal display 62 for providing a visual readout of distance 54 between caliper jaws 42 and 44. Electronic or digital calipers of the kind exemplified by caliper 20 are well known in the measurement field. A preferred form of caliper 20 is distributed by the Fowler Company under the trademark MAX-CAL.

Figure 4:
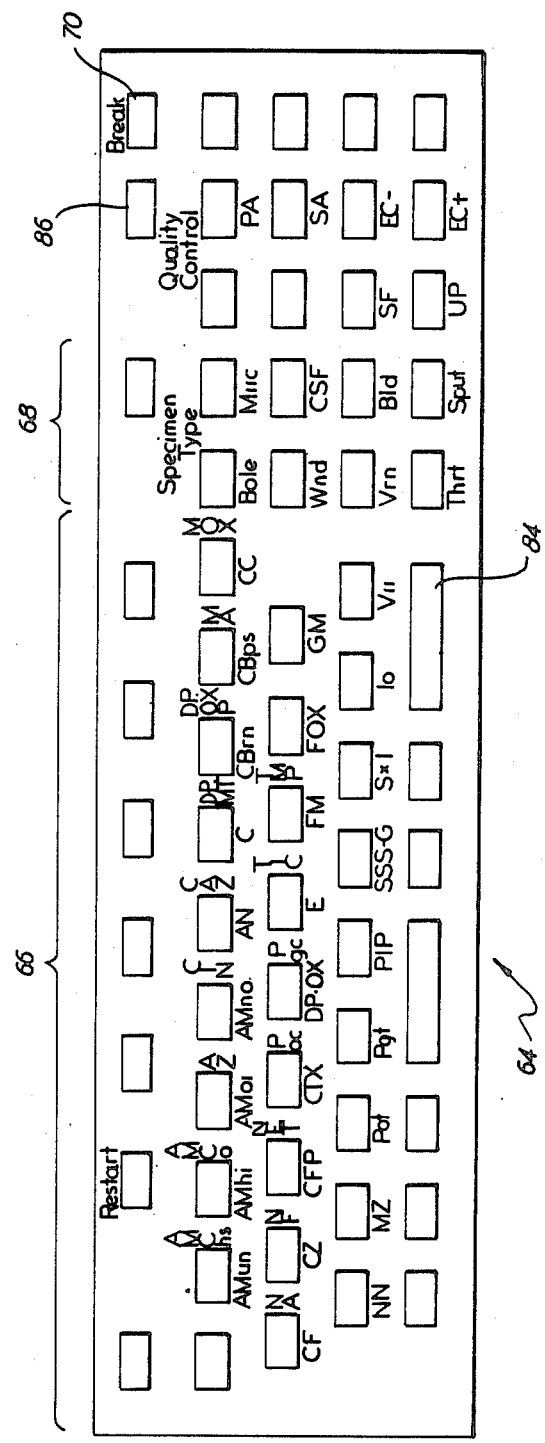
FIG. 4 is a plan view, on an enlarged scale, of the keyboard shown in FIG. 1.

As illustrated in FIGS. 1, 3 and 4, microprocessor 14 is provided with an input device in the form of a keyboard 64. The keyboard is provided with a first array of keys 66 each assigned to at least one antimicrobial drug and a second set of keys 68 assigned to respective body fluids, such as the bile, blood ("BLD"), urine ("URN") and cerebral spinal fluid ("CSF") or to a type of body tissue such as throat tissue ("THRT") or wounded tissue ("WND").

In order to use an apparatus in accordance with the invention, a number of steps common to the conventional agar diffusion technique are initially undertaken. A sample of a bacterium under study, e.g., from a throat smear or a urine sample, is spread upon a surface of an agar medium in a petri dish 70 (see FIG. 1). A plurality of small disks 72 each carrying a known quantity of a respective antimicrobial drug, e.g., a drop of a solution containing the drug in a predetermined concentration, are then placed on the surface of the agar medium upon which the bacterium sample has been disposed. The bacterium sample is then incubated for approximately 5 or 6 hours during which time the bacteria grow and multiply to form a culture on the surface of the agar. The bacteria fail to grow within circular inhibition zones 74 surrounding each antimicrobial-carrying disk 72. Each bacteria-growth inhibition zone 74 has a diameter 76 determined by the degree of susceptibilty of the bacterium under study to the antimicrobial drug contained in the respective disk 72.

It is to be understood that the drug-carrying solutions may be placed into receptacles in the form of holes or wells in the agar medium, rather than being received by absorbant paper disks placed on the surface of the agar. This technique is usually used when determining an unknown drug concentration, as described in detail hereinafter.

During incubation of the bacteria culture, the antimicrobial drugs on the disks (or holes) 72 diffuse outwardly from the disks through the agar nutrient medium. The density of the molecules of any particular drug varies inversely with the distance from the disk carrying the drug. In addition, the density of the respective antimicrobial drug is essentially constant along any circular locus of points which is concentric with the respective disk, provided that the diameter of the circle falls within a certain range.

Figure 5:
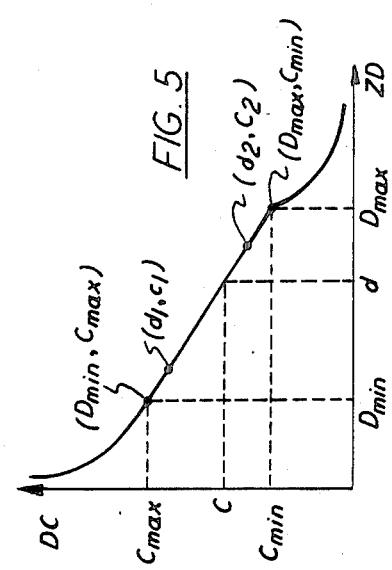
FIG. 5 is a graph showing the inverse mathematical relationship between zone diameter, as measured by the disk diffusion technique, and drug concentration.

As illustrated in FIG. 5, the concentration DC of an antimicrobial drug as determined by the broth dilution test is a linear function of zone diameter ZD as determined by the agar diffusion method, within a zone diameter range between a minimum diameter $D_{min}$ maximum diameter $D_{max}$. If a zone diameter 76 for a particular antimicrobial drug falls outside of the range for that drug, i.e., is less than $D_{min}$ or greater than $D_{max}$, the drug concentration corresponding to the zone diameter cannot be accurately and reliably estimated.

The memory of computer or microprocessor 14 contains, for each antimicrobial drug represented on keyboard 64, two pairs of digitally encoded values $(d_1, c_1)$ and $(d_2, c_2)$ which define the linear relationship between the zone diameter, as measured by the agar diffusion method, and the drug concentration, as measured by the dilution method. These ordered pairs of values may be the endpoints $(D_{min}, C_{max})$ and $(D_{max}, C_{min})$ of the straight line defining the mathematical relation between zone diameter ZD and concentration DC of the drug in accordance with dilution method standards.

In order to measure the zone diameters 76 of the various bacterium-growth inhibition zones 74 on the surface of the nutrient medium in dish 70, the dish is disposed over the transparent portion 28 of inclined plate 26. The dish is held in position over the circular transparency 28 by the lip 30 surrounding the transparency.

Toggle switch 38 is pivoted to an "on" position, whereby light sources 34 and 36, as well as other components of the apparatus, such as printer 16, are connected to an A-C power line via a power cord (not illustrated). The computer is then turned on by pressing a button 70 (see FIG. 4). Caliper 20 is calibrated by first closing the caliper jaws 42 and 44 (or, alternatively, 46 and 48) and then continuously depressing pushbutton 60 while briefly depressing and the releasing another key or pushbutton 74. While the first pushbutton 60 is depressed, a message will appear on display 62 of caliper 20, e.g., the message "OP-2," indicating that the caliper is calibrated to 0. Another key 76 on caliper carriage 50 is then pushed to switch the caliper display from inches to millimeters.

Upon the completion of the calibration of the caliper, microprocessor 14 generates a message on a liquid crystal display 82 (see FIGS. 1 and 3), indicating the initiation of a quality control sequence or routine. In order to test the quality of the drug-carrying disks 72 on the surface of the nutrient medium in dish 70, a multiplicity of drug-carrying disks (not illustrated) taken from the same batches as disks 72 are placed on the surface of a nutrient medium produced with the agar in dish 70. The surface of the nutrient medium in the test batch of drug-carrying disks is provided with a sample of a control bacterium (e.g., *Escherichia Coli* specific quality control strains B-lactamase negative or positive) having known susceptibilities to the various antimicrobial drugs. Upon the completion of an incubation period, the sizes of bacteria-growth inhibiton zones surrounding the drug-carrying disks are measured by caliper 20. The values of the measured zone diameters are transmitted in digital form to microprocessor 14 from caliper 20.

Microprocessor 14 checks the measured zone diameters against memorized standard zone diameters corresponding to the drugs being tested and to the selected control microbe. If a measured zone diameter differs from the associated memorized diameter by more than a predetermined limit, the microprocessor indicates a quality fault to the technician via display 82 or via a print-out from printer 16.

Upon the termination of the quality control procedure, microprocessor 14 generates a message on display 82 requesting the entry of the specimen type, i.e., the type of body fluid or tissue from which the bacterium sample on dish 70 originated. In response to the request, the technician pushes the appropriate key in array 68 (FIG. 4) and then presses an "enter" key 84. If the specimen type is unknown, a "miscellaneous" entry (button "misc") may be made.

Upon the entry of the specimen type, the microprocessor 14 displays a sequence of prompting messages on display 82, requesting the entry of additional information such as the name of the patient, the body organ or tissue site under investigation and the name of the microorganism being tested for drug susceptibility. In order to have a response entered into the memory of the microprocessor, it is necessary to press the "enter" button upon completing the typing of the respective entry.

Microprocessor 14 then asks for the name of the antimicrobial drug whose corresponding bacteria-growth inhibition zone 74 on dish 70 is to to be measured. In response to this query, the technician pushes the appropriate button in array 66. If the wrong drug key is pressed, the technician may correct the error by closing the jaws of caliper 20 and pushing button 60 on caliper carriage 50. The next drug is then identified by pushing the correct button in array 66.

To measure the size of a bacteria-growth inhibition zone, the technician rotates screw 52, while simultaneously comparing the spacing 54 between jaws 42 and 44 or 46 and 48 to the diameter 76 of the zone 74 being measured. Upon detecting equality between the jaws spacing 54 and zone diameter 76, the technician presses pushbutton 60 on caliper carriage 50, thereby inducing the automatic transmission to microprocessor 14 of a signal coding the measured value d of the zone diameter 76.

In response to the signal from caliper 20, microprocessor 14 automatically calculates a drug concentration c (see FIG. 5) corresponding to the measured value d of the zone diameter. This calculated drug concentration c represents the minimum inhibitory concentration of the antimicrobial drug on the disk 72 at the center of the measured inhibition zone 74, i.e., the least concentration of the drug required to substantially inhibit or prevent the growth of the bacterium whose drug susceptibility is being measured.

In response to the signal from caliper 20, microprocessor 14 also calculates inhibitory quotients for a plurality of body fluids. An inhibitory quotient for a particular body fluid is the ratio of the usual concentration of the antimicrobial drug supportable or achievable in that body fluid to the calculated minimum inhibitory concentration. The memory of microprocessor 14 stores in digital form the usual concentrations of each antimicrobial drug in each body fluid.

The body fluids for which microprocessor calculates inhibitory quotients depend on the specimen type entered into microprocessor 14 at the commencement of the susceptibility measurement phase. If, for example, urine is the selected specimen type, microprocessor 14 computes inhibitory quotients for each antimicrobial drug with respect to urine and with respect to blood.

Microprocessor 14 actuates printer 16 to print the name of each drug being tested, the respective minumum inhibitory concentration and the associated inhibitory quotients computed by the microprocessor. These results may be printed after each test specimen or after the measurement of inhibition zone diameters on a number of different dishes. If a maximum number of test dishes is exceeded, the printer is automatically activated. Upon the completion of the zone diameter measurements, the technician turns microprocessor 14 off by first pressing key 70 and then pressing an "off" key 86.

The apparatus illustrated in FIGS. 1 and 3 may also be used to determine an unknown concentration of an antimicrobial drug. First, one prepares a culture plate bearing a sample of a control bacterium which is susceptible to the drug under test. Into holes in the agar nutrient medium are then placed preselected volumes of a plurality of solutions, the preselected volumes having various known amounts of the antimicrobial being tested. Generally, it is preferable to select several known drug concentrations and to dispense into the holes in the agar nutrient medium or onto absorbant paper disks, several repeats for each known concentration. A plurality of additional holes or disks carrying the unknown concentration are also placed in communication or contact with the nutrient medium.

Upon the termination of an incubation period, caliper 20 is used to measure the zone diameters corresponding to all of the holes which have received a preselected volume of a drug-containing solution, the microprocessor 14 being informed via keyboard 64 of the identity of drug corresponding to each inhibition zone diameter fed into microporocessor from caliper 20. Microprocessor 14 is programed to automatically calculate an average inhibition zone diameter for each known concentration of the drug under study and for the unknown concentration of the drug. From the averages of the known concentrations a regression function is computed, thereby establishing a linear relationship between zone diameter and drug concentration with respect to the antimicrobial drug under test and the bacterium used as the sample. The unknown concentration of the drug is then calculated from the linear regression function using standard mathematical techniques.

What follows is an operating program for microprocessor 14 written in the BASIC source code language:

```
10:ARUN

20:REM PROGRAM NAME: BIOGRAM  850120:1415

40:REM  THIS PROGRAM CALC MIC'S FROM ZONE DIA. DISK DIFFUSION  TEST

50:REM  COPYRIGHT 1984****DAVID GIBBS***

60:CLEAR

80:DIM DRG$(43)*4,IS$(5)*1,CS$(43)*1,TYP$(13)*6

81:DIM SP$(17)*15

82:DIM CO$(17)*20

83:DIM RG$(17)*20

84:DIM G(17),SN$(17)*6

100:DIM CODE(8,43),VL(5),KV(3,43),QC (6,43),O(17,12),P(17,12)

102:R=17

108:LOCK :WAIT 20

110:USING "&&&&&&&&&&&&&&&&&&&&&&&&" PRINT "WELCOME TO BIOGRAM-WAIT"
120:DATA "AMPI","AMPI","AMPI","AMPI"

140:DATA "AMIK","CLOR","CARB","CARB","CLND"

160:DATA "CEPH","CZOL","CFOP","CTAX","OXAC"

180:DATA "ERTH","NTRO","CFOX","GENT","TOBR"

200:DATA "MZLO","PENG","PENG","PIPR","SULF"

220:DATA "TMSZ","TETR","VANC","AUGM","AUGM"

240:DATA "AZLO","CNOX","CTZD","METH","OXAC"

250:DATA "CMAN","MOXL","NALD"

260:DATA "NAFC","NTIL","PENG","PENG"
```

280:DATA "TICR","TRIM"

300:FOR I=1TO 43:READ DRG$(I):NEXT I

320:DATA "A","A","A","A","C","A","C","C","B","B","A","B","C", "B","A","A"

340:DATA "B","A","B","D","A","A","D","A","A","A","D","C","C", "D","B","C"

360:DATA "B","B","B","C","A","B","A","A","C","A"

370:FOR I=1TO 43:READ CS$(I):NEXT I

380:DATA 46,7,.25,30,35,500,10,3,0,0,0,0,0,0,0,0

400:DATA 16,16,.25,24,35,500,10,3

420:DATA 8,19,.12,30,35,500,10,3,61,12,2,23,25,200,5,5

440:DATA 40,10,3,29,15,100,3,10,240,10,4,30,250,1000,50,20

460:DATA 240,10,6,30,250,1000,50,20,3.5,11.5,21,15,30,40,0

480:DATA 64,10,.7,30,70,500,10,.7,64,10,.7,30,110,1000,50,0

500:DATA 230,10,1.1,29,250,1000,2000,0,84,10,.6,30,80,1000,15,10

520:DATA 7,7,.2,25,70,500,2.5,1,40,9,.25,26,1.4,200,800,0

540:DATA 64,14,.15,35,0,50,0,0,48,10,.9,32,70,1000,100,1.5

560:DATA 18,11,.5,24,6,50,2,1,18,11,.8,22,6,50,2,1

580:DATA 240,12,3.5,27,190,2000,100,0,10,14,.12,30,115,300,15,6

600:DATA 12,8,.12,29,115,300,15,6,33,0,12,1.8,29,190,2000,100,0

620:DATA 350,12,100,17,0,0,0,0,152,1,0,8,23,30,100,30,15

640:DATA 16,12,.6,26,2.2,100,15,0,20,9,1,15,10,100,3,3

660:DATA 64,8,2,26,4,500,5,0,64,8,2,26,4,500,5,0
680:DATA 256,13,4,29,190,2000,100,0,64,14,16,19,0,300,0,0

700:DATA 64,11,1.1,29,100,1000,20,2

720:DATA 15,7,.5,24,80,1000,30,1,0,0,0,0,0,0,0,0

740:DATA 32,10,.6,30,70,1000,100,0

760:DATA 69,12,.84,30,100,1000,60,10,44,8,2,28,0,200,0,0

780:DATA 7,7,.2,25,70,150,40,2,56,10,1,25,5,50,2,0

800:DATA 16,14,.25,20,115,300,15,6,0,0,0,0,0,0,0,0

820:DATA 128,11,4,27,190,2000,50,20

840:DATA 16,10,4,16,0,0,0,0

860:FOR I=1TO 43:FOR J=1TO 8:READ CODE(J,I):NEXT J:NEXT I

```
880:DATA "BILE","WOUND","URINE","THROAT","MISC","CSF","BLOOD","SPUTUM"
900:DATA "EC-","SA ","PA ","EC+","SF"
920:FOR I=1TO 13:READ TYP$(I):NEXT I
940:DATA 16,22,27,35,0,0,16,22,27,35,0,0
960:DATA 16,22,27,35,0,0,16,22,27,35,0,0,19,26,20,26,18,26
980:DATA 21,27,19,26,0,0,23,29,0,0,1,8,24,23,29,0,0,18,24
1000:DATA 0,0,24,30,0,0,17,22,29,37,0,0,23,29,29,35,0,0
1020:DATA 20,34,24,33,23,29,29,35,2,5,31,18,22,0,0,18,24,0,0
1040:DATA 0,0,22,30,0,0,20,25,10,22,0,0,23,29,23,29,0,0
1060:DATA 19,26,19,27,16,21,10,26,1,9,20,19,25,23,29,0,0,19,25
1080:DATA 0,0,26,37,0,0,0,0,26,37,0,0,24,30,0,0,25,33
1100:DATA 18,26,24,32,0,0,24,32,24,32,24,32,18,25,19,20,0,0
1120:DATA 0,0,15,13,0,0,19,25,20,36,18,22,13,25,28,30,18,22
1140:DATA 0,0,0,0,24,39,26,32,0,00,25,32,16,20,22,29
1160:DATA 0,0,17,22,0,0,0,0,10,24,0,0
1180:DATA 24,39,26,34,0,0
1190:DATA 28,35,10,24,17,25
1200:DATA 22,28,0,0,0,0,0,0,16,22,0,0,22,30,22,31,17,23
1220:DATA 0,0,26,37,0,0,0,0,26,37,0,0
1240:DATA 24,30,0,0,21,27,21,29,21,28,0,0
1260:FOR I=1TO 43:FOR J=1TO 6:READ QC(J,I):NEXT J:NEXT I
1290:DATA 12,13,14,0,0,20,17,39,100,22,29,30,15,16,17,13,17,18
1300:DATA 18,22,23,14,16,17,15,16,17,15,17,18,15,17,18,16,20,21,1,5,22,23
1320:DATA 11,12,13,14,17,18,15,16,1,7,15,17,18,13,14,15,13,14,15,1,3,15,16
1340:DATA 20,27,28,0,0,29,15,17,10,13,16,17,11,15,16,15,18,13,14,15,1,
        13,16,17,11,15,16,15,13,10,11,12
1360:DATA 0,0,20,14,17,10,15,17,18,15,18,19,15,17,18,10,13,14
1380:DATA 0,0,20,15,17,10,15,22,23,14,18,19
1390:DATA 11,12,13,13,14,15
1400:DATA 15,39,100,0,0,20,12,14,15,11,15,16
```

```
1420:FOR I=1TO 43:FOR J=1TO 3:READ KV(J,I):NEXT J:NEXT I
1430:INPUT "PEN NO. (0-3)";Y
1432:COLOR Y:H=0:F=0
1434:GOTO 1620
1440:SETDEV
1460:CSIZE 1:LPRINT :LPRINT
1480:X$=STR$ TIME
1500:IF TIME >99999THEN 1540
1520:X$="0"+X$
1540:MO$=LEFT$ (X$,2):D$=MID$ (X$,3,2):H$=MID$(X$,5,2):M$=MID$(X$,8,2)
1560:DA$=MO$+"/"+D$+"/1984"
1580:I$="TIME: "+H$+":"+M$
1590:A$="&&&&&&&&&&&&&&&"
1600:LPRINT USING A$;DA$
1605:C=1
1610:GOTO 3585
1620:WAIT 0:CC=0
1640:M=0:I$=""
1650:USING "&&&&&&&&&&&&&&&&&&&&&&&"
1660:PRINT "SPEC TYPE/QC BUG/6 PRINT"
1680:I$=INKEY$
1700:PRINT I$
1720:IF I$<>""THEN GOTO 1745
1740:GOTO 1640
1745:IF I$="6"AND G(H)>0PRINT USING A$;"WAIT-PRINTING"
1750:IF I$="6"AND G(H)>0GOTO 1440
1760:IF I$="7"THEN LET M=1
1780:IF I$="4"THEN LET M=2
1800:IF I$="1"THEN LET M=3
1820:IF I$="0"THEN LET M=4
```

```
1840:IF I$="8"THEN LET M=5

1860:IF I$="5"THEN LET M=6

1880:IF I$="2"THEN LET M=7

1900:IF I$="."THEN LET M=8

1920:IF I$="/"THEN LET M=11

1940:IF I$="*"THEN LET M=10

1960:IF I$="-"THEN LET M=9

1980:IF I$="+"THEN LET M=12

2000:IF I$="3"THEN LET M=13

2040:IF M=0THEN PAUSE

2060:IF M=0THEN GOTO 1640

2062:H=H+1

2063:IF H>RPAUSE "MAX-PRINTING":GOTO 1440

2064:G(H)=M

2080:SN$(H)="9":SP$(H)=" ":CO$(H)=" ":RG$(H)=" "

2090:IF M>8THEN GOTO 2210

2100:INPUT "ENTER SPECIMEN NO.";SN$(H)

2120:INPUT "ENTER PATIENT NAME";SP$(H)

2140:INPUT "ENTER COMMENT (IF ANY)";CO$(H)

2180:IF M>8THEN GOTO 2210
2200:INPUT "ENTER ORGANISM NAME";RG$(H)

2205:A=0

2210:WAIT 0:KK=0

2212:USING A$

2220:N=0:K$=" "

2280:IF A=12THEN PAUSE "12 MAXIMUM" :GOTO 1620

2240:PRINT "PRESS DRUG";" OR 9 NEXT TEST"

2260:K$=INKEY$

2280:PRINT K$

2300:IF K$<>""THEN GOTO 2330

2320:GOTO 2220
```

```
2330:IF K$="="THEN LET KK=27:WAIT 60:PRINT K$:WAIT 0
2332:IF K$="9"AND M<9THEN GOTO 1620
2333:IF K$="9"AND M>8THEN LF 5
2334:IF K$="="THEN GOTO 2220
2336:IF K$="9"AND M>8THEN GOTO 1620
2360:IF K$="W"THEN LET N=1+KK
2380:IF K$="E"THEN LET N=2+KK
2400:IF K$="R"THEN LET N=3+KK
2420:IF K$="T"THEN LET N=4+KK
2440:IF K$="Y"THEN LET N=5+KK
2480:IF K$="U"THEN LET N=6+KK
2500:IF K$="I"THEN LET N=7+KK
2520:IF K$="O"THEN LET N=8+KK
2540:IF K$="P"THEN LET N=9+KK
2560:IF K$="A"THEN LET N=10+KK
2580:IF K$="S"THEN LET N=11+KK
2600:IF K$="D"THEN LET N=12+KK
2660:IF K$="F"THEN LET N=13+KK
2640:IF K$="G"THEN LETN=14+KK
2660:IF K$="H"THEN LET N=15+KK
2680:IF K$="J"THEN LET N=16+KK
2690:IF KK=27THEN GOTO 3320
2700:IF K$="K"THEN LET N=17
2720:IF K$="L"THEN LET N=18
2722:IF K$="Z"THEN LET N=19
2760:IF K$="X"THEN LET N=20
2780:IF K$="C"THEN LET N=21
2800:IF K$="U"THEN LET N=22
2820:IF K$="B"THEN LET N=23
2840:IF K$="N"THEN LET N=24
2860:IF K$="M"THEN LET N=25
```

```
2880:IF K$="("THEN LET N=26

2900:IF K$=")"THEN LET N=27

3320:IF N=0THEN PAUSE

3330:IF N=0THEN LET KK=0

3340:IF N=0THEN GOTO 2210

3350:WAIT 60:PRINT DRG$ (N)

3400:REM INPUT "ENTER ZONE DIA.";ZD

3420:REM GOTO 3580

3440:SETDEV :OUTSTAT 0

3480:SETCOM 2400,2,N,1

3500:SETDEV KI

3520:INPUT $"PRESS CALIPER BUTTON"; Z$

3540:S1=VAL (LEFT$ (Z$,3)):ZD=VAL (MID$ (Z$,7,8)) :SIM$=MID$ (Z$,16,1):SETDEV

3560:IF SIM$="I"LET ZD=ZD*25.4:LET SIM$="M"

3580:PAUSE "ZONE DIA.=";USING "#####" ;ZD;"MM"

3581:IF ZD<5THEN PAUSE "REENTER": GOTO 2210

3582:IFM 0>8THEN GOTO 4280

3584:A=A+1:O(H,A)=N:P(H,A)=ZD:GOTO 2210
3585:IF E>0GOTO 3587

3586:INPUT "HOW MANY COPIES";E

3587:USING "&&&&&&&&&&&&&&&&&&&&&&&&&&"

3588:PRINT "WAIT TILL (FINISHED)SHOWS"

3590:FOR Q=1TO H:B=1

3592:N=O(Q,B):M=G(Q)

3595:IF CODE(1,N)=0THEN GOTO 3984

3600:L1=LOG (CODE(3,N)):L2=LOG (CODE(1,N))

3620:M1=((3.322*(L1-L2))/(CODE(4,N)-CODE(2,N)))

3640:MIC=2*(M1*ZD-M1*(CODE(2,N))+3.322*LOG (CODE(1,N)))

3660:K=5

3680:FOR J=2TO 5:VL(J)=CODE(K,N)/MIC:K=K+1:IS$(J)=" ":NEXT J

3700:IS$(1)=" ":VL(1)=MIC

3720:IMIC=INT ((MIC+.005)*100):MIC= IMIC/100
```

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the descriptions and illustrations herein are proffered by way of example to facilitate comprehension of the invention and should not be construed to limit the scope thereof.

What is claimed is:

1. A medical testing apparatus utilizable with an agar diffusion technique for determining a quantitative drug concentration parameter related to the size of a bacteria-growth inhibition zone, wherein said zone surrounds a drug-carrying receptacle in communication with a nutrient medium bearing a bacteria culture, said apparatus comprising in combination:
   distance measuring means for measuring a linear dimension of the bacteria-growth inhibition zone and for generating a signal coding the measured value of said linear dimension;
   computing means for automatically calculating, in response to said signal, the quantitative drug concentration parameter; and
   coupling means for operatively connecting said distance measuring means to said computing means to enable automatic transmission of said signal to said computing means, said distance measuring means being provided with means including a manually actuatable switch for inducing transmission of said signal over said coupling means to said computing means.

2. The medical testing apparatus recited in claim 1 wherein said parameter is a minimum inhibitory concentration of a drug on said disk, said minimum inhibitory concentration being the least concentration of said drug which effectively prevents the growth of the bacteria of said culture, said computing means including memory means for storing in digitally encoded form sufficient information to define a linear relationship between the size of the bacteria-growth inhibition zone for said drug, as defined by said linear dimension, and the concentration of said drug in solution.

3. The medical testing apparatus recited in claim 2 wherein said memory means also stores in digitally encoded form a usual achievable concentration of said drug in a preselected type of body fluid, said computing means being programmed to automatically calculate, in response to said signal, an inhibitory quotient defined as a ratio of said usual achievable concentration to said minimum inhibitory concentration.

4. The medical testing apparatus recited in claim 3 wherein said linear relationship is limited to a range of values of said linear dimension, said range being defined at one end by a minimum value and at an opposite end by a maximum value of said linear dimension, said computing means including limit recognition means for determining when the measured value of said linear dimension is less than said minimum value and when the measured value of said linear dimension is greater than

```
3740:FOR J=2TO 6:IVL=INT ((VL(J)+.005)*100):VL(J)=IVL/100:NEXT J

3760:IF MIC >=CODE(3,N)THEN GOTO 3000

3780:K=3:VL(I)=CODE(3,N):IS$(1)="(":GOTO 3840

3800:IF INT (MIC+.55) <=CODE(1,N) THEN GOTO 3900

3820:K=1:VL(1)=CODE(1,N):IS$(1)=">"

3840:L=5:FOR J=2TO 5:JL(J)=CODE(L,N))/CODE(K,N):L=L+1:IF K=1THEN LET IS$(J)="<"

3860:IF K=3THEN LET IS$(J)=">"

3880:IVL=INT ((VL(J)+.005)*100):VL$(J)=IVL/100:NEXT J

3900:IVL=INT ((VL(1)+.05)*10):VL(1)=IVL/10

3920:FOR J=2TO 5

3940:IVL=INT ((VL(J)=.05)*10):VL(J)=IVL/10

3960:IF IS$(J)="<"AND VL(J)< =.1THEN LET IS$(J)=" " :VL(J)=0

3980:NEXT J

3982:GOTO 4000

3984:FOR J=1TO 5:VL(J)=0.:IS$(J)=" "

3986:NEXT J
```

```
4000:KB$="R"

4010:IF KV(1,N)=0THEN GOTO 4040

4020:IF ZD>=KV(1,N)-.5THEN LET KB$= "I"

4040:IF ZD>KV(2,N)+.5AND ZD>=KV(3,N)-.5THEN LET KB$="S"

4080:IF N=3AND KB$="I"THEN LET KB$="MS"

4100:IF N=4AND KB$="I"THEN LET KB$= "MS"

4140:IF N=12AND KB$="I"THEN LET KB$ ="MS"

4180:IF N=13AND KB$="I"THEN LET KB$=MS"

4200:IF N=21AND KB$="I"THEN LET KB$ ="MS"

4220:IF N=36AND KB$="I"THEN LET KB$="MS"

4240:IF N=40AND KB$="I"THEN LET KB$="MS"

4260:GOTO 4540

4280:IF M=5THEN LET Q1=1

4300:IF M=10THEN LET Q1=3

4320:IF M>10THEN LET Q1=5

4340:INV$="INVALID ORGANISM"

4360:IF M=12AND N<28THEN GOTO 4436

4382:IF M=12AND N>29THEN PRINT INV$; "REENTER"

4384:IF M=12AND N>23THEN GOTO 1620

4386:IF M=11AND N=25THEN GOTO 4436

4388:IF M=11AND N=28THEN GOTO 4436

4390:IF M=11AND N=29THEN GOTO 4436

4400:IF M=13AND N<>25THEN GO TO 4436

4430:IF QC(Q1,N)=0THEN GOTO 4436

4434:GOTO 4440

4436:PRINT INV$;"REENTER"

4438:GOTO 1620

4440:Q2=Q1+1:ZL=ZD-QC(Q1,N):ZH=ZD-QC(Q2,N):TST$="NO"

4460:IFZL> -.5AND ZH<.5THEN LET TST$="OK"

4470:D=0
```

```
4480:IF ZL<OTHEN LET D=ZL

4500:IF ZL>OTHEN LET D=ZH

4540:A3$="&&&":B0$="&&&&&&&&"

4560:IF M>8THEN GOTO 4980

4562:IF CC=1THEN GOTO 4664

4580:LPRINT USING "&&&&&&";SN$(2);USING A$;SP$(Q)

4600:LPRINT TYP$(M)

4620:D2$="&&&&&&&&&&&&&&&&&&&&&&&&&&&&&&&"

4640:LPRINT USING D2$;CO$(Q)

4660:LPRINT RS$(Q)

4662:B$= " ";S$= "        "

4664:S1$=B$+IS$(1)+S$:S2$=B$+IS$(2)+S$:S3$=B$+IS$(3)+S$

4666:S4$=B$+IS$(4)+G$:S5$=B$+IS$(8)+S$

4668:IF CC=1THEN GOTO 4750

4670:CC=1

4675:USING "&&&&&&&&&&"

4680:IF M=2OR M=4OR M=5OR M>6THEN LPRINT "   DRUG   KB";" MIC  SIQ";"         $"

4700:IF M=3THEN LPRINT "   DRUG   KB";" MIC     SIQ";"    SIQ    $"

4720:IF M=1THEN LPRINT "   DRUG   KB";" MIC     SIQ";"    BIG    $"

4740:IF M=6THEN LPRINT "   DRUG   KB ";" MIC     SIQ";"    CIG    $"

4750:IF M=3THEN LET VX=VL(3):SX$=S3$

4752:IF M=1THEN LET VX=VL(4):SX$=S4$

4754:IF M=6THEN LET VX=VL(5):SX$=S5$

4760:A2$="&&":A1$="&":N3$="####.#":N4$="#####.#":A7$="&&&&&&&":N6$="######.#"

4788:IF M=2OR M=4OR M=5OR M>6THENGOTO 4820

4800:GOTO 4900

4820:LPRINT USING B0$;DRG$(N);USINGA2$;KB$;USING A7$;S1$;S2$;"";USING A1$;CS$(N)

4840:LF -1

4860:LPRINT TAB 12;USING N3$;VL(1);TAB 19;VL(2)

4870:GOTO 4946
```

```
4900:LPRINT  USING B0$;DRG$(N);USINGA2$;KB$;USING A7$;S1$;S2$;SX$;USING
     A1$;B$;B$;CS$(N)

4920:LF -1

4940:LPRINT TAB 12;USING N3$;VL(1);TAB 19;VL(2);TAB 24;USING N6$;VX

4946:LPRINT :B=B+1

4947:IFB>12THEN GOTO 4950

4948:IF P(Q,B)>4THEN GOTO 3592

4950:LF 3:CC=0

4952:IF Q<HTHEN LPRINT USING A$;DA$

4953:NEXT Q

4954:LPRINT USING D2$;D2;D2$

4955:F=F+1

4956:IF F<ETHEN GOTO 1440

4957:E=0:H=0:A=0

4958:INPUT "FINISHED -PUSH(ENTER)";X$

4960:GOTO 1620

4980:CSIZE 1

4981:IF CC=OTHEN LPRINT "    QC":USING A3$;TYPE$(M)

4982:CC=1

5000:LPRINT USING B0$;DRG$(N);USING"###.##";ZD;"    ;USING A3$;TST$;USING"+###";D

5020:LPRINT :H=P:GOTO 2210

5040:END
``` said maximum value, for defining said minimum inhibitory concentration to be greater than an upper limiting value when the measured value of said linear dimension is less than said minimum value and to be less than a lower limiting value when the measured value of said linear dimension is greater than said maximum value and for further defining said inhibitory quotient to be less than a lower boundary value when said minimum inhibitory concentration is greater than said upper limiting value and to be greater than an upper boundary value when said minimum inhibitory concentration is less than said lower limiting value.

5. The medical testing apparatus recited in claim 4, wherein said memory means stores in digitally encoded form usual achievable concentrations of said drug in a multiplicity of different body fluids, further comprising instruction input means including a keyboard operatively coupled to said computing means for instructing said computing means to automatically calculate an inhibitory quotient for each of a plurality of said body fluids, each inhibitory quotient representing a ratio between the respective usual achievable concentration and said minimum inhibitory concentration.

6. The medical testing apparatus recited in claim 5, wherein said memory means stores, in digitally encoded form, for each of a multiplicity of different antimicrobial drugs, information defining a linear relationship between (a) the size of a bacteria-growth inhibition zone about a disk carrying the respective antimicrobial drug on the culture-bearing medium and (b) the concentration of the respective antimicrobial drug in solution, said memory means further storing in digitally encoded form usual achievable concentrations of each of said antimicrobial drugs in the multiplicity of different body fluids, said input means being operatively connected to said computing means for instructing said computing means to automatically calculate in response to signals from said distance measuring means, a minimum inhibitory concentration and a plurality of inhibitory quotients for a selected one of said antimicrobial drugs.

7. The medical testing apparatus recited in claim 6 further comprising printer means operatively connected to said computing means for printing data including names of drugs, minimum inhibitory concentrations and inhibitory quotients.

8. The medical testing apparatus defined in claim 2 wherein said distance measuring means includes an electronic caliper.

9. The medical testing apparatus defined in claim 1 wherein said distance measuring means includes an electronic caliper.

10. The medical testing apparatus recited in claim 1 wherein said parameter is a concentration of a selected drug in a sample solution.

11. The medical testing apparatus recited in claim 1 wherein said bacteria-growth inhibition zone is circular and said linear dimension is a diameter of said zone.

12. The medical testing apparatus recited in claim 1, further comprising a housing containing a light source and having means for supporting a dish containing said medium so that light from said source shines through said medium substantially uniformly over said surface, further comprising a frame for supporting said computing means, said housing and said frame being detachably connectable to one another.

13. A method using an agar diffusion technique for determining a quantitative drug concentration parameter related to the size of a bacteria-growth inhibition zone, wherein said zone surrounds a drug-carrying receptacle in communication with a nutrient medium bearing a bacteria culture, said method comprising the steps of:
   manipulating an electronic caliper so that the spacing of a pair of jaws of said caliper is approximately equal to a linear dimension of the bacteria-growth inhibition zone surrounding the drug-carrying receptacle; and
   operating said caliper to automatically generate and transmit, to a computing means, a signal coding the linear dimension measured by said step of manipulating, said computing means being programmed for automatically calculating, in response to said signal, the quantitative drug concentration parameter.

14. The method recited in claim 13 wherein said parameter is a minimum inhibitory concentration of a drug, said minimum inhibitory concentration being the least concentration of said drug which effectively prevents the growth of the bacteria of said culture.

15. The method recited in claim 14 wherein said computing means includes memory means for storing in digitally encoded form sufficient information to define a linear relationship between said linear dimension of the bacteria-growth inhibition zone for said drug and the concentration of said drug in solution, said computing means automatically calculating said minimum inhibitory concentration from said linear relationship and said signal.

16. The method recited in claim 15 wherein said memory means also stores in digitally encoded form a usual achievable concentration of said drug in a preselected type of body fluid, said computing means being programmed to automatically calculate in response to said signal an inhibitory quotient defined as a ratio of said usual achievable concentration to said minimum inhibitory concentration.

17. The method recited in claim 16 wherein said linear relationship is limited to a range of values of said linear dimension, said range being defined at one end by a minimum value and at an opposite end by a maximum value of said linear dimension, said computing means including limit recognition means for determining when the measured value of said linear dimension is less than said minimum value and when the measured value of said linear dimension is greater than said maximum value, for defining said minimum inhibitory concentration to be greater than an upper limiting value when the measured value of said linear dimension is less than said minimum value and to be less than a lower limiting value when the measured value of said linear dimension is greater than said maximum value, and for further defining said inhibitory quotient to be less than a lower boundary value when said minimum inhibitory concentration is greater than said upper limiting value and to be greater than an upper boundary value when said minimum inhibitory concentration is less than said lower limiting value.

18. The method recited in claim 17 wherein said memory means stores in digitally encoded form usual achievable concentrations of said drug in a multiplicity of different body fluids, further comprising the step of instructing said computing means to automatically calculate an inhibitory quotient for each of a plurality of said body fluids, each inhibitory quotient representing a ratio between the respective usual achievable concentration and said minimum inhibitory concentration.

19. The method recited in claim 16 wherein said linear relationship is limited to a range of values of said linear dimension, said range being defined at one end by a minimum value and at an opposite end by a maximum value of said linear dimension, said computing means including limit recognition means for determining when the measured value of said linear dimension is less than said minimum value and when the measured value of said linear dimension is greater than said maximum value, for defining said minimum inhibitory concentration to be greater than an upper limiting value when the measured value of said linear dimension is less than said minimum value, and for defining said minimum inhibitory conbcentration to be less than a lower limiting value when the measured value of said linear dimension is greater than said maximum value.

20. The method recited in claim 14 wherein said computing means includes memory means for storing in digitally encoded form, for each of a multiplicity of different antimicrobial drugs, information defining a linear relationship between (a) the size of a bacteria-growth inhibition zone about a disk carrying the respective antimicrobial drug on a culture-bearing medium and (b) the concentration of the respective antimicrobial drug in solution, said memory means further storing in digitally encoded form usual achievable concentrations of each of said antimicrobial drugs in a multiplicity of different body fluids, further comprising the step of instructing said computing means to automatically calculate in response to signals from said electronic caliper a minimum inhibitory concentration and a plurality of inhibitory quotients for a selected one of said antimicrobial drugs, each of said inhibitory quotients being a ratio of a respective usual achievable concentration for a respective body fluid to the minimum inhibitory concentration.

21. The method recited in claim 20, further comprising the step of printing data including names of drugs, minimum inhibitory concentrations and inhibitory quotients.

22. The method recited in claim 13 wherein said parameter is an unknown concentration of a selected drug in a sample solution.

23. The method defined in claim 22, further comprising the steps of (a) measuring linear dimensions of bacteria-growth inhibition zones surrounding a plurality of holes carrying respective known amounts of said selected drug, (b) generating and transmitting to said computing means from said electronic caliper signals coding the measured linear dimensions, and (c) operating said computing means to automatically calculate in response to said signals a regression of said known amounts as a function of measured linear dimensions, said computing means automatically calculating a value for said unknown concentration from said regression and from a signal from said electronic caliper coding a measured linear dimension of a bacteria-growth inhibition zone surrounding a hole carrying the unknown concentration of said selected drug.

24. The method recited in claim 13 wherein said bacteria-growth inhibition zone is circular and said linear dimension is a diameter of said zone.

25. A method for determining a minimum inhibitory concentration of an antimicrobial drug necessary to substantially prevent growth of a predetermined kind of bacterium, said method comprising the steps of:
disposing a sample of the bacterium on a surface of a nutrient medium;
placing on said surface a small disk bearing a predetermined amount of the antimicrobial drug;
incubating the sample of said bacterium to produce a culture of said bacterium on said surface;
manipulating an electronic caliper so that the spacing of a pair of jaws of said caliper is approximately equal to a linear dimension of a bacteria-growth inhibition zone surrounding said disk on said surface, thereby measuring the size of said zone;
actuating said caliper to automatically generate and transmit, to a computing means, a signal coding the measured linear dimension of said zone, said computing means being programmed to automatically calculate, in response to said signal from said caliper, the minimum inhibitory concentration of said antimicrobial drug required to substantially prevent growth of said bacterium, said computing means including memory means for storing, in digitally encoded form, sufficient information to define a linear relationship between said linear dimension of the bacteria-growth inhibition zone for said antimicrobial drug and the concentration of said antimicrobial drug in solution.

26. A method for determining an unknown concentration of an antimicrobial drug in a solution, said method comprising the steps of:
disposing, on a surface of a nutrient medium, a sample of a bacterium known to be susceptible to the antimicrobial drug;
placing preselected volumes of a plurality of solutions in respective first holes in said nutrient medium, each preselected volume having a respective preselected amount of said antimicrobial drug;
placing in a second hole in said nutrient medium a preselected volume of the solution with an unknown concentration of said antimicrobial drug;
incubating the sample of said bacterium to produce a culture thereof on said surface;
manipulating an electronic caliper so that the spacing of a pair of jaws of said caliper is approximately equal to a linear dimension of a bacteria-growth inhibition zone surrounding one of said holes in said nutrient medium, thereby measuring the size of said zone;
actuating said caliper to automatically generate and transmit, to a computing means, a signal coding the measured linear dimension of said zone;
repeating said steps of manipulating and actuating for each hole in said nutrient medium;
generating and transmitting to said computing means signals coding the preselected amounts of said antimicrobial drug placed in said first holes, said computing means being programmed to automatically generate a regression of said preselected amounts as a function of the sizes of the respective zones on said surface of said medium and to calculate a value for said unknown concentration in accordance with said regression.

27. A medical testing apparatus, connectable to computing means such as a computer or microprocessor, for utilizing an agar diffusion technique to determine a quantitative drug concentration parameter related to the size of a bacteria-growth inhibition zone, wherein the zone surrounds a drug-carrying receptacle in communication with a nutrient medium bearing a bacteria culture, said apparatus comprising in combination:
distance measuring means for measuring a linear dimension of the bacteria-growth inhibition zone and for generating a signal coding the measured value of said linear dimension; and
coupling means including an interface operatively connected to said distance measuring means and operatively connectable to the computing means for transmitting said signal from said distance measuring means to said computing means.

28. The medical testing apparatus defined in claim 27 wherein said distance measuring means includes an electronic caliper.

29. The medical testing apparatus defined in claim 28, further comprising holding means for supporting a receptacle containing the nutrient medium and light emission means for shining light through the nutrient medium upon a disposition of said receptacle on said holding means, said interface being attached to said holding means.

* * * * *